(12) United States Patent
Krishna et al.

(10) Patent No.: US 9,084,989 B2
(45) Date of Patent: Jul. 21, 2015

(54) ENHANCEMENT OF ELECTRON SCAVENGING BY WATER-SOLUBLE FULLERENES

(75) Inventors: Vijay Krishna, Gainesville, FL (US);
Brij M. Moudgil, Gainesville, FL (US);
Benjamin L. Koopman, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 1183 days.

(21) Appl. No.: 13/000,765

(22) PCT Filed: Jun. 24, 2009

(86) PCT No.: PCT/US2009/048467
§ 371 (c)(1),
(2), (4) Date: Jan. 21, 2011

(87) PCT Pub. No.: WO2010/008889
PCT Pub. Date: Jan. 21, 2010

(65) Prior Publication Data
US 2011/0112232 A1 May 12, 2011

Related U.S. Application Data

(60) Provisional application No. 61/075,258, filed on Jun. 24, 2008.

(51) Int. Cl.
| | |
|---|---|
| *B60C 1/00* | (2006.01) |
| *B01J 35/00* | (2006.01) |
| *B82Y 10/00* | (2011.01) |
| *B82Y 30/00* | (2011.01) |
| *B82Y 40/00* | (2011.01) |
| *C01B 31/02* | (2006.01) |
| *H01L 51/00* | (2006.01) |
| *B01J 21/06* | (2006.01) |
| *B01J 23/06* | (2006.01) |

(52) U.S. Cl.
CPC ............... *B01J 35/004* (2013.01); *B82Y 10/00* (2013.01); *B82Y 30/00* (2013.01); *B82Y 40/00* (2013.01); *C01B 31/0206* (2013.01); *C01B 31/0213* (2013.01); *H01L 51/0047* (2013.01); *B01J 21/063* (2013.01); *B01J 23/06* (2013.01); *Y02E 10/549* (2013.01)

(58) Field of Classification Search
USPC ........................................................ 524/424
See application file for complete search history.

(56) References Cited

U.S. PATENT DOCUMENTS

| | | |
|---|---|---|
| 5,294,732 A | 3/1994 | Chiang et al. |
| 6,020,523 A | 2/2000 | Chiang |

FOREIGN PATENT DOCUMENTS

JP    2007-176899    7/2007

OTHER PUBLICATIONS

Guirado-Lopez, R.A. et al., "Structural and optical properties of highly hydroxylated fullerenes: Stability of molecular domains on the C60 surface," *The Journal of Chemical Physics*, 2006, pp. 154312-1-154312-10, vol. 125.
Husebo, L.O. et al., "Fullernols Revisited as Stable Radical Anions," *Journal American Chemical Society*, 2004, pp. 12055-12064, vol. 126.
Kamat, P.V. et al., "Photochemistry on Semiconductor Surfaces. Visible Light Induced Oxidation of $C_{60}$ on $TiO_2$ Nanoparticles," *J. Phys. Chem. B*, 1997, pp. 4422-4427, vol. 101.
Krishna, V. et al., "Enhancement of titanium dioxide photocatalysts by water-soluble fullerenes," *Journal of Colloidal and Interface Science*, 2006, pp. 166-171, vol. 304.
Li, J. et al., "$C_{60}$ Fullerol Formation catalysed by Quaternary Ammonium Hydroxides," *J. Chem. Soc., Chem. Commun.*, 1993, pp. 1784-1785, Issue 23.
Rodriguez-Zavala, J.G. et al., "Stability of Highly OH-Covered $C_{60}$ Fullerenes: Role of Coadsorbed O Impurities and of the Charge State of the Cage in the Formation of Carbon-Opened Structures," *J. Phys. Chem. A*, 2006, pp. 9459-9468, vol. 110.
Xing, G. et al., "Influences of Structural Properties on Stability of Fullerenols," *J. Phys. Chem. B*, 2004, pp. 11473-11479, vol. 108.

*Primary Examiner* — Ling Choi
*Assistant Examiner* — Thuy-Ai Nguyen
(74) *Attorney, Agent, or Firm* — Saliwanchik, Lloyd & Eisenschenk

(57) ABSTRACT

Polyhydroxyfullerenes (PHFs) having enhanced electron scavenging capabilities have a ratio of non-hydroxyl functional groups to hydroxyl functional groups that is less than or equal to 0.3. When combined with a semiconductor photocatalyst, such as titanium dioxide nanoparticles, the PHFs provide a photocatalyst for degradation of chemical and biological contaminates with an efficiency of at least twice that of titanium dioxide nanoparticles free of PHFs. The PRFs are included in these catalysts at a weight ratio to titanium dioxide of about 0.001 to about 0.003, whereas significantly lower and higher ratios do not achieve the highly improved photodegradation capability. PHFs outside of the desired structure are shown to be of little value for photodegradation, and can be inhibiting to the photocatalytic activity of $TiO_2$. The enhanced electron scavenging PHFs can be employed as a component of materials for solar cells, field effect transistors, and radical scavengers.

16 Claims, 5 Drawing Sheets

ENHANCEMENT OF ELECTRON SCAVENGING BY WATER-SOLUBLE FULLERENES

CROSS-REFERENCE TO RELATED APPLICATIONS

This application is the U.S. national stage application of International Patent Application No. PCT/US2009/048467, filed Jun. 24, 2009, which claims the benefit of U.S. Provisional Application Ser. No. 61/075,258, filed Jun. 24, 2008, which is hereby incorporated by reference herein in its entirety, including any figures, tables, or drawings.

GOVERNMENT SUPPORT

The subject matter of this application has been supported by a research grant from the National Science Foundation under grant number EEC-9402989. Accordingly, the government has certain rights in this invention.

BACKGROUND OF THE INVENTION

Fullerenes are well known as omnidirectional electron acceptors. Due to the spherical and symmetrical nature of the more common fullerenes, such as $C_{60}$ known as Buckminster fullerene, electrons can be accepted at any point on the fullerene cage, which differs from typical organic electron scavengers that accept electrons only at specific sites of the scavenger molecule. This non-specific electron accepting ability of fullerenes has been exploited for various applications including electrochemical sensors, photochemical cells, therapeutics, photocatalysis, and electronic devices such as n-type and field effect transistors.

Pristine and functionalized fullerenes have been employed as electron acceptors in electrochemical sensors for detection of various organo- or bio-analytes such as dopamine and nandrolone. Typically, the electrochemical sensor comprises an electrode upon which fullerenes have been coated. The sensing results due to the transfer of electrons to the fullerene by a negatively charged analyte upon application of an electric field.

For photochemical and solar cells, typically fullerenes are employed as metal porphyrin-fullerene combinations or in other forms such as dyads. For a metal porphyrin-fullerene combination the metal porphyrin generates electrons upon absorption of photons. The electrons are then scavenged by the conjugated fullerenes to promote the flow of current through a circuit. In addition to metal porphyrins, other photoactive materials that can be combined with fullerenes for use in photochemical cells include $TiO_2$, ZnO and various organic dyes.

Fullerenes scavenge free radicals, such as superoxide, by accepting electrons from the free radical. These antioxidant properties of fullerenes have been applied for therapeutic uses, such as the treatment of various diseases such as Alzheimer and Parkinson disease and for reducing the side-effects of cancer treatment. Fullerene comprising compositions have been commercialized as anti-ageing cosmetics.

Fullerenes have been used in combination with semiconductor photocatalysts. Semiconductor photocatalysts are employed for the destruction of environmentally hazardous chemicals and bioparticulates, as these materials can be a cost-effective means to achieve complete mineralization of these environmental hazards without generation of toxic byproducts. For example, titanium dioxide has been commercially applied as a self-cleaning coating on buildings and glass materials. However, such applications have been limited by the low quantum efficiency of these photocatalysts. In photocatalysis, with a photocatalyst such as titanium dioxide, electron-hole pairs are generated in the semiconductor upon irradiation with ultraviolet light. Some of the photo-generated electrons and holes migrate to surfaces, where they undergo redox reactions to generate reactive species such as hydroxyl radicals. However, the photo-generated electrons and holes can also undergo recombination, which reduces the quantum efficiency of photocatalysis.

Several attempts have been made to separate the photogenerated electrons and holes to reduce recombination. Titanium dioxide photocatalysts have been conjugated or doped with electron scavenging agents such as metals or organic molecules. Numerous organic molecules have been conjugated with titanium dioxide for applications that include solar cells and visible light photocatalysis. Platinum, gold and silver metals are often employed as scavenging agents, generally due to their high conductivity, although conflicting results have been reported. Another class of conductors examined is carbon nanotubes. For example, anatase coated multiwall carbon nanotubes (MWNT) achieved twice the efficacy of a commercial photocatalytic $TiO_2$ (Degussa P25) for inactivation of bacterial endospores. It was hypothesized that the photo-generated electrons are scavenged by the MWNT. These approaches involve processing to conjugate or dope the $TiO_2$ or scavenging agent and have resulted in a relatively high cost to produce the modified photocatalysts.

As indicated above, fullerenes such as $C_{60}$, because of their unique electronic properties, have been examined for combination with semiconductor photocatalysts. Kamat et al., "Photochemistry on Semiconductor Surfaces. Visible Light Induced Oxidation of $C_{60}$ on $TiO_2$ Nanoparticles", *J. Phys. Chem. B,* 1997, 101 (22) 4422-7, discloses the transfer of photo-generated electrons from titanium dioxide to fullerenes with ethanol/benzene mixed solvent. Fullerenes are extremely hydrophobic, limiting their use for enhancing photocatalysis in aqueous environments. The water solubility of fullerenes improves by forming hydroxyl groups on the surface of the fullerenes. However, addition of hydroxyl groups to the fullerene structure modifies the electronic properties of the fullerenes. The toxic effects attributed to fullerenes are not observed for the hydroxylated form of fullerenes. Rather, polyhydroxyfullerenes are able to reduce oxidative stress on cells by scavenging reactive oxygen species and have been patented as therapeutics as, for example: Chiang et al., U.S. Pat. No. 5,994,410.

Recently Polyhydroxyfullerenes (PHFs) were reported for enhancement of the photocatalytic activity of titanium dioxide ($TiO_2$). Krishna et al., "Enhancement of Titanium Dioxide Photocatalysis with Water-Soluble Fullerenes", *J. Colloid and Interface Sci.,* 2006, 304, 166-71, demonstrated that hydroxylated fullerenes display electron accepting properties and can be employed to scavenge photogenerated electrons from $TiO_2$, thereby increasing the rate of photocatalysis. However, not all PHFs enhance the photocatalytic activity of $TiO_2$. Hence, identification of the PHF structures that promote $TiO_2$ photocatalytic activity is needed.

BRIEF SUMMARY OF THE INVENTION

The present invention is directed to polyhydroxyfullerenes ($C_{20}$ to $C_{500}$ PHFs) having an average ratio of non-hydroxyl functional groups to hydroxyl functional groups that is less than or equal to 0.3. PHFs in which this ratio is higher provide significantly less efficiency and can impair the performance of materials that require electron scavenging.

A photocatalyst comprising $TiO_2$ nanoparticles and PHFs can be used for degradation of chemical or bacteriological contaminants. The photocatalyst can be a suspension in an aqueous solvent and is readily formulated as an aqueous suspension. The catalyst can be prepared from commercially available $TiO_2$ nanoparticles with a diameter of about 2 to about 100 nm in diameter. Incorporating the PHFs at very low levels, 0.001 to 0.003 grams of PHFs per g of $TiO_2$, forms an effective photocatalyst.

Additionally, the invention is directed to a method of photochemically decontaminating a surface or a fluid medium in contact with the surface. The fluid medium can be a liquid or a gas, where the contaminants are either dissolved or suspended in the medium. The surface is rendered photochemically active by providing a photocatalyst as described above to the surface. Irradiating the photocatalyst with ultraviolet or visible light promotes the degradation of the contaminant. Irradiation can be the exposure of the photocatalyst to a light source. The light source can be natural light such as sunlight, or can be provided by an artificial lamp. For example UVA irradiation can be provided from an ultraviolet lamp.

In an embodiment of the invention, the novel PHFs can be employed as an active film for a heterojunction organic solar cell when combined with a conjugated polymer. Such polymers include polythiophene, substituted polythiophene, polyvinylenephenylene substituted polyvinylenephenylene, polybenzothiadiazole, substituted polybenzothiadiazole, polypyrroles, substituted polypyrroles or copolymers thereof. In another embodiment of the invention, the enhanced electron scavenging PHFs can be used as the organic semiconductor for an organic thin-film field effect transistor (FET) where, when PHFs are used alone, is an n-channel semiconductor. Alternately, the PHFs can be combined with a conducting polymer that is a p-channel semiconductor to create an ambipolar device. In another embodiment, the PHFs can be used as a radical scavenger, functioning as an antioxidant or radioprotectant.

DETAILED DESCRIPTION OF THE INVENTION

Figure 1:
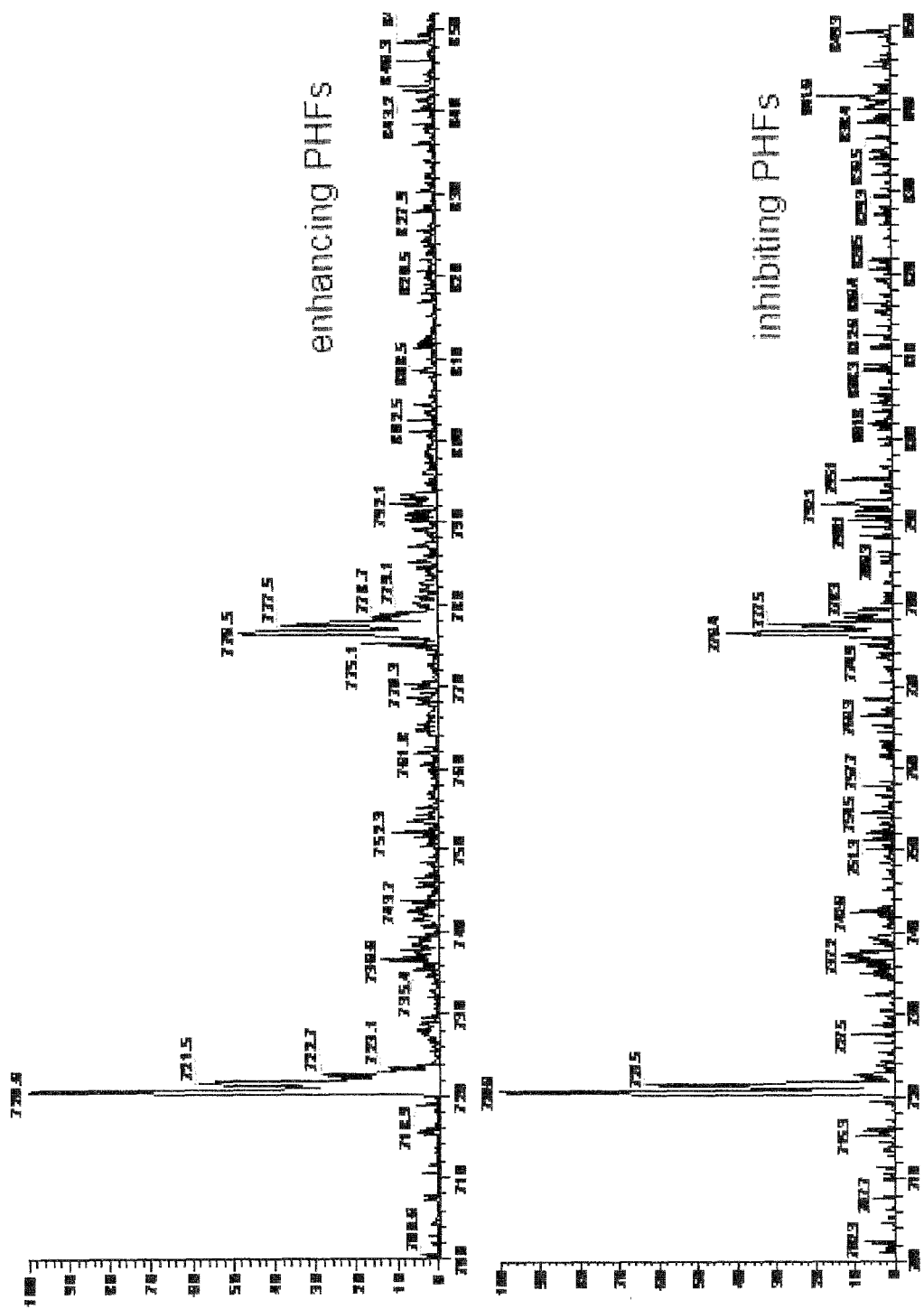
FIG. 1 shows atmospheric pressure chemical ionization mass spectra (APCI-MS) of PERC PHFs (enhancing) and BuckyUSA PHFs (inhibiting).

The present invention is directed to PHF compositions that result in an enhanced electron scavenging ability. In embodiments of the invention the enhanced electron scavenging PHFs are combined with other materials or employed in devices that exploit the enhanced electron scavenging PHFs. The functionality of PHF influences its electron scavenging ability. PHFs commonly contain functional groups such as hydroxyl, hemiketal, epoxide and carbonyl groups that modify the electronic properties of the PHFs. It was discovered that PHFs which have a low ratio (< or =0.3) of non-hydroxyl functional groups to hydroxyl functional groups have enhanced electron scavenging ability, whereas PHFs that display a ratio higher than 0.3 have little or no electron scavenging ability. It was also discovered that PHFs where the weight loss to temperatures of about 1,000° C. is less than about 55% exhibit enhanced electron scavenging ability, whereas PHFs which display weight loss of more than 80% have little or no electron scavenging ability and can even promote inhibition of processes requiring an electron scavenger. PHF compositions that achieve higher electron scavenging can enhance processes such as photocatalysis.

PHFs can be of a single size or can be mixtures of different fullerene sizes. The fullerene cage can be $C_{28}$, $C_{32}$, $C_{44}$, $C_{50}$, $C_{58}$, $C_{60}$, $C_{70}$, $C_{84}$, $C_{94}$, $C_{250}$, $C_{540}$, or any other fullerene. The PHFs have an average of about 1.25 to 3 C atoms per OH group, which is equivalent to about 27 to about 48 OH groups on a $C_{60}$ cage. The PHFs are often $C_{60}$ molecules due to their commercial availability, but $C_{70}$, $C_{82}$ or their mixtures or other PHFs can be used in various embodiments of the invention. The PHFs have C—C single bonds that can be observed by Fourier transform infrared spectroscopy (FTIR). Other functional groups are primarily carbons of a hemiketal and carbonyl structure. PHFs can also contain epoxy groups and ester groups. As the PHFs of the present invention are water soluble, they can be incorporated into devices that can exploit their enhanced electron scavenging capabilities and permit fabrication or use in an aqueous environment. Hence, the enhanced electron scavenging PHFs can be used in biological systems or permit processing from aqueous solution for electronic devices.

In an embodiment of the invention, a photocatalytic composition of scavenging enhanced PHFs with semiconducting photocatalyst nanoparticles comprises a ratio of PHF/photocatalyst of about 0.001 to about 0.003 in aqueous suspension at about pH 6. In an embodiment employing $TiO_2$ as the photocatalyst, the photocatalytic activity of the inventive composition is at least two times the photocatalytic activity of $TiO_2$, absent the PHFs. The $TiO_2$ concentrations can be from about 10 to about 100 mg/L. The $TiO_2$ nanoparticles can range from about 2 to about 100 nm in diameter. The PHFs have C—C single bonds that are observable by Fourier transform infrared spectroscopy (FTIR). Other functional groups are primarily carbons of a hemiketal and carbonyl structure. PHFs can also contain epoxy groups and ester groups as long as the ratio of non-hydroxyl functional groups to hydroxyl functional groups is 0.3 or less.

Among the semiconducting photocatalysts that can be used for the practice of the invention are particles of titanium oxide, anatase titanium oxide, brookite titanium oxide, strontium titanate, tin oxide, zinc oxide, iron oxide, and mixtures thereof. Particles can range from about 2 to 500 nm maximum cross section or diameter. Particles can range from 2 to 100 nm in average diameter or cross section. The particles can be spherical or any other shape. Another embodiment of the invention including semiconducting photocatalysts with PHFs is a method to decontaminate a surface or a fluid in contact with the surface. The surface is treated with semiconducting photocatalytic nanoparticles with the proper proportions of scavenging enhancing PHFs or other functional fullerenes. The fluid in contact with the photocatalyst can be a liquid, generally an aqueous solution, or a gas. Irradiation of the photocatalyst results in the decomposition of chemical or biological contaminates. The irradiation source can be ultraviolet (UV) or visible and can be from a natural or artificial source. For example, sunlight can be used for the irradiation of the photocatalyst or light from a lamp can be directed to the photocatalyst. The system can be employed on exterior surfaces for passive cleaning in air ventilation systems or in water purification systems where the photocatalyst is restricted to a desired region to function as a decontaminating agent. The fluids can be forced into contact with the photocatalyst and recirculated to promote partial to complete decontamination of the fluid.

In other embodiments of the invention the electron scavenging enhanced PHFs as an electron acceptor are combined with an electron donor to form a heterojunction organic solar cell's active film. The electron donor can be a low band gap conjugated polymer, for example polythiophene, substituted polythiophene, polyvinylenephenylene substituted polyvinylenephenylene, polybenzothiadiazole, substituted polybenzothiadiazole, polypyrroles, substituted polypyrroles and regular or random copolymers thereof. The active film can also have included nanoparticulate semiconducting photocatalyst, such as $TiO_2$. Conjugated polymers that are water soluble due to substitution can be combined with the water soluble PHFs to fabricate an active film of a heterojunction organic solar cell.

In other embodiments of the invention, the electron scavenging enhanced PHFs are used as the organic semiconductor of n-channel organic thin-film field effect transistors (FETs). In another embodiment of the invention, the electron scavenging enhanced PHFs can be combined with p-channel organic components, such as polythiophenes, to form ambipolar organic field effect transistors.

In another embodiment of the invention, the electron scavenging enhanced PHFs can be employed as a radical scavenger or antioxidant. The electron scavenging enhanced PHFs can be employed as a radioprotectant for an organism that experiences exposure to ionizing radiation, such as X-rays.

Materials and Methods

Two types of polyhydroxyfullerenes, both synthesized by an alkali route, were tested: 1) PHF from BuckyUSA (BuckyUSA PHF) and 2) PHF synthesized in the laboratory (PERC PHF). The laboratory synthesis was carried out in a manner derived from that disclosed in Li et al. *J. Chem. Soc.-Chem. Commun.*, 1993, 1784. A solution of non-derivatized fullerenes was prepared by adding 80 mg of $C_{60}$ (95%, BuckyUSA, Houston Tex.) to 60 mL of benzene (HPLC grade, Fisher). A mixture of 2 mL of NaOH solution (1 g/mL) and 0.3 mL of tetra butyl ammonium hydroxide (40% solution) was prepared in a separate Erlenmeyer flask. The fullerene solution was added to the alkali-surfactant solution under vigorous stirring. The stirring was stopped after 30 minutes and the mixture was allowed to phase separate. The top clear phase was decanted and the remaining slurry was stirred with an additional 12 mL of deionized water for 24 hours. The mixture was filtered through Whatman 40 filter paper and the filtrate was concentrated to 5 mL in a vacuum oven at 60° C. The resultant slurry was washed four times with 50 mL of methanol by alternate centrifugation (5000 g, 10 min) followed by resuspension in methanol. After the final wash, PHF were suspended in 20 mL of methanol and dried under vacuum at 60° C. The mass of PHF obtained was 120 mg. The PHF samples were analyzed with atmospheric pressure chemical ionization (APCI) mass spectroscopy (MS) (ThermoFinnigan, San Jose, Calif.).

Both the BuckyUSA and PERC PHFs were characterized by Diffuse Reflectance Infrared Fourier Transform (DRIFT) and x-ray photoelectron spectroscopy (XPS). DRIFT experiments were carried out with Thermo Electron Magna 760 unit with potassium bromide as the background. XPS experiments were performed with Kratos Analytical Surface Analyzer XSAM 800 in survey and multiplex mode. The carbon 1s (C1s) spectrum was subjected to peak fitting analysis using Grams 7.01 software (Thermo Fisher Scientific, Waltham, Mass.) to determine the oxidation states of carbon.

Characterization of PHF Samples

Mass Spectroscopy

Mass spectroscopy was employed to investigate the stability of the fullerene cages of the BuckyUSA and PERC PHF samples. The portions of the MS spectra in the range of 700-850 m/z for the two samples are presented in FIG. 1. In both samples, the base fullerene ($C_{60}$) peak at 720.6 m/z is present at a relative intensity of 100, indicating that the fullerene cage is intact.

FTIR Analysis

Figure 2:
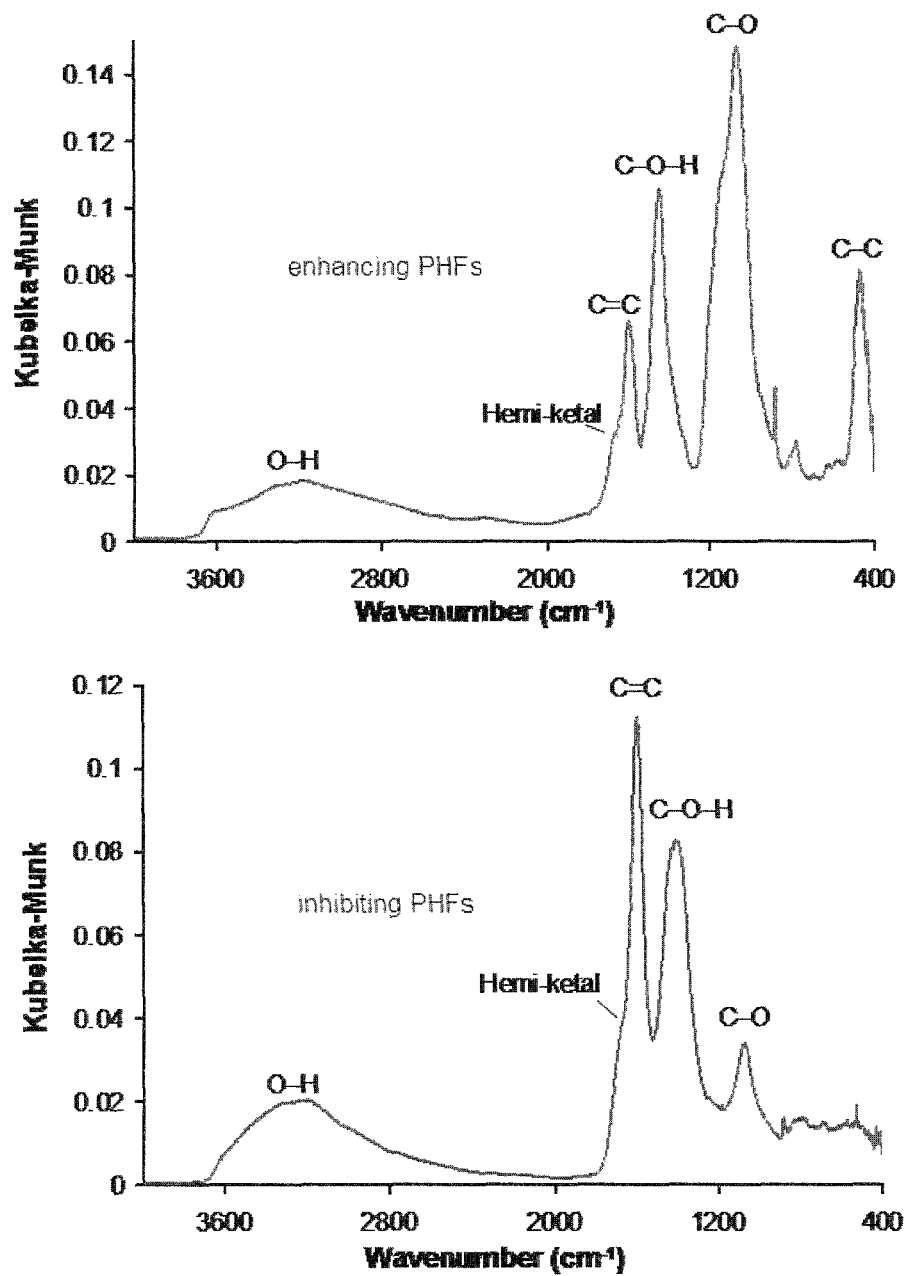
FIG. 2 shows Fourier Transform. Infrared Spectra of PERC PHFs (enhancing) and BuckyUSA PHFs (inhibiting).

FTIR spectroscopy has been employed previously to identify functional groups present on a fullerene cage. The FTIR-DRIFT spectra for BuckyUSA and PERC PHF are presented in FIG. 2. The PERC PHF exhibits five peaks at 3300, 1591, 1450, 1062, 881 and 471 wavenumbers along with shoulders at 1661, 1357 and 1165 wavenumbers. The BuckyUSA PHF has peaks at 3300, 1595, 1408 and 1074 wavenumbers with a shoulder at 1680 cm$^{-1}$. The vibrational modes of PHF were assigned to FTIR peaks of PHF based on the information obtained from a Gaussian simulation and the literature, as shown in Table 1, below. The peak at 1591 was not observed in the simulation and was ascribed to C=C vibrations as reported in the literature. The shoulders at 1658 cm$^{-1}$, 1357 cm$^{-1}$ and 1165 cm$^{-1}$ were attributed to hemiketal, epoxides and esters respectively.

TABLE 1

Assignments of FTIR peaks for PERC and BuckyUSA PHF based on results from Gaussian simulation of $C_{60}(OH)_{24}$ and literature.

| Vibration modes | Peak Location in cm$^{-1}$ based on Gaussian Simulation | Peak Location in cm$^{-1}$ based on Literature | Peak Assignments in cm$^{-1}$ based on Gaussian simulation and/or literature PERC PHF | BuckyUSA PHF |
|---|---|---|---|---|
| O—H stretching | 3450 | 3420, 3430, 3410, 3300 | 3300 | 3300 |
| Hemiketal | — | 1658 | 1661 | 1680 |
| C=C stretching | — | 1595, 1600, 1593, 1585 | 1591 | 1595 |
| C—O—H bending | 1450 | 1392, 1412 | 1450 | 1408 |
| Epoxides | — | 1376 | 1357 | — |
| C—O stretching | 1070 | 1084, 1070, 1065 | 1062 | 1074 |
| Esters | — | 1197 | 1165 | — |
| C—C | — | 490 | 471 | — |

Figure 3:
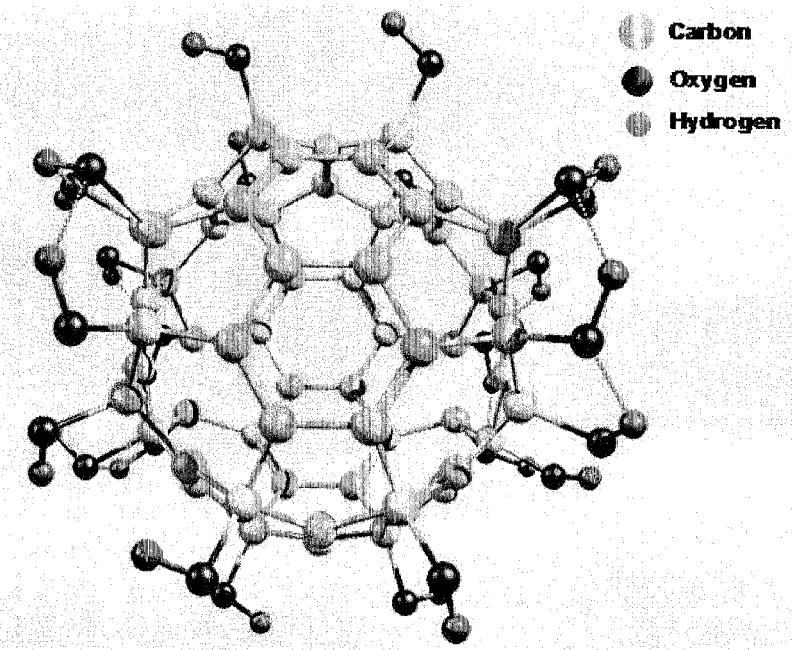
FIG. 3 shows the structure of a $C_{60}(OH)_{24}$ molecule calculated by Gaussian simulation.

Semi-empirical computation (PM3) has been employed in the literature for structure optimization of various hydroxylated fullerenes and possible stable isomers are reported in the literature. However, no reports are present on theoretical prediction of vibrational peaks for hydroxylated fullerenes. Therefore, hybrid quantum chemical computations were carried out to identify the vibration modes responsible for experimentally observed FTIR peaks. For ease of simulation, 24 hydroxyl groups and no carbonyl, hemiketal and epoxide functionalities on the PHF were assumed. The structure optimization and vibration spectrum generation were performed with hybrid quantum-chemical basis set (B3LYP 6-31G*). The optimized structure, as shown in FIG. 3, is similar to the reported $C_{60}(OH)_{24}$ structure obtained by a semi-empirical quantum-chemical optimization (PM3), as reported in Slanina et al., *Proceedings of the Electrochemical Society*, 1996, 96, 987. The hydroxyl groups are present as intramolecularly hydrogen bonded islands on fullerene cage, similar to the results found in the literature. The average C—O and O—H bond lengths are 1.43 and 0.98 Å, respectively, and the average C—O—H bond angle is 107°. These results are similar to the values obtained with PM3 optimization for $C_{60}(OH)_{26}$ by Guirado-Lopez et al., *J. Chem. Phys.*, 2006, 125. Additionally, weak intramolecular hydrogen bonding was observed with an average bond length of 1.78 Å, which is similar to the hydrogen bond length in water.

Figure 4:
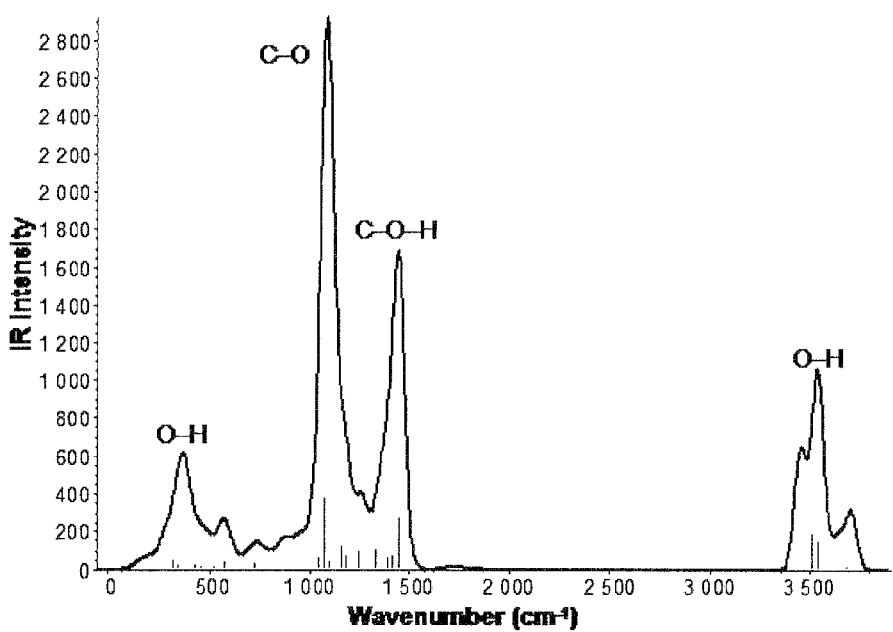
FIG. 4 shows a vibrational spectrum for $C_{60}(OH)_{24}$ calculated by Gaussian simulation.

The vibration spectrum generated for $C_{60}(OH)_{24}$ with the B3LYP 6-31 G* basis set is presented in FIG. 4, with wavenumbers increasing from left to right on x axis. The simulated FTIR peak exhibits four major peaks. The broad peak at 3450 $cm^{-1}$ originates from O—H stretching. The peak at 1450 $cm^{-1}$, 1070 $cm^{-1}$ and 370 $cm^{-1}$ represents C—O—H bending, C—O stretching and O—H rocking vibrations, respectively.

Both samples of PHF have hemiketal and epoxide groups in addition to hydroxyl groups, as revealed by FTIR and XPS analysis. This is consistent with reports in the literature. Rodriguez-Zavala et al., *J. Phys. Chem. A*, 2006, 110, 9459, discloses theoretical studies on hydroxylated fullerenes with different numbers of epoxide groups, where the presence of epoxide groups on hydroxylated fullerenes can have significant effects on their structure and electronic and optical properties.

XPS Analysis

PHFs have hemiketal, epoxide and sometimes carbonyl functional groups in addition to hydroxyl groups. Therefore, extensive characterization of PHF as well as determination of its empirical formula is necessary to compare the properties. Unfortunately, there is a lack of consistency in literature on techniques employed for determining the empirical molecular formula of PHF. Three common methodologies employed are elemental analysis, thermo gravimetric analysis (TGA) and X-ray photoelectron spectroscopy (XPS). It is known that the presence of residue can influence the empirical formula determined by TGA and elemental analysis. Therefore XPS data was used to determine the empirical formulas for PERC and BuckyUSA PHF samples.

Figure 5:
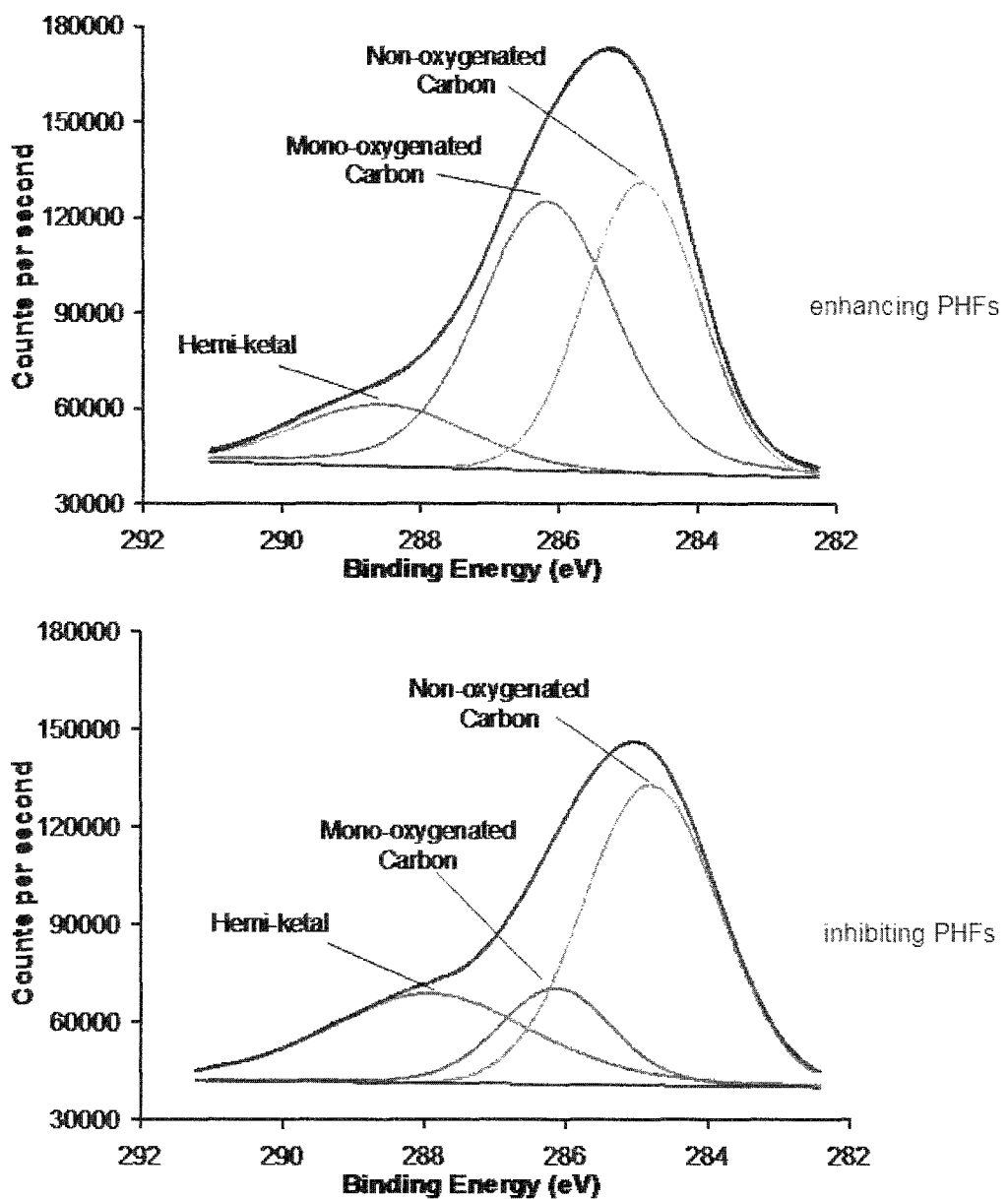
FIG. 5 shows the C1s signals in XPS spectra of PERC PHFs (enhancing) and BuckyUSA PHFs (inhibiting). Each spectrum is deconvoluted into three signals for non-oxygenated, mono-oxygenated and di-oxygenated carbons.

XPS analysis indicated the presence of C, O and Na in both PERC and BuckyUSA PHF samples. The relative atomic concentrations determined for each element are provided in Table 2, below. The C1s region was deconvoluted as three Gaussian curves revealing the presence of three oxidation states of carbon, as shown in FIG. 5, which is in agreement with the literature. Since no carbonyl peak was present in FTIR spectra, the highest oxidation state was assumed to be due to hemiketal structure as revealed from FTIR. The curve fitting analysis of the three Gaussian peaks was performed for the C1s spectrum of PERC and BuckyUSA PHF to calculate the relative concentration of each carbon oxidation state (Table 3). The relative concentration of mono-oxygenated carbon is three times higher in PERC PHF than BuckyUSA PHF.

TABLE 2

Elemental Composition of PHFs by XPS

| Element | Relative Non-Hydrogen Atomic Concentration in Percent | |
|---|---|---|
| | PERC PHF | BuckyUSA PHF |
| Carbon | 61.23 | 47.33 |
| Oxygen | 28.44 | 33.82 |
| Sodium | 10.33 | 18.85 |

TABLE 3

Peak Position and Elemental Composition of PHFs by XPS Analysis

| Oxidation State of Carbon | Peak Position in eV | | Relative Concentration in % | |
|---|---|---|---|---|
| | PERC PHF | BuckyUSA PHF | PERC PHF | BuckyUSA PHF |
| Non-oxygenated | 284.8 | 284.8 | 40.2 | 57.1 |
| Mono-oxygenated | 286.16 | 286.14 | 47.1 | 16.1 |
| Di-oxygenated | 288.55 | 287.91 | 12.7 | 26.8 |

The relative atomic concentrations of C, O and Na and along with concentrations of mono- and di-oxygenated states of carbon were employed to deduce the composition of PHF using the assignment as per Husebo et al., *J. Amer. Chem. Soc.*, 2004, 126, 12055. The molecular formula for PERC PHF was calculated as $C_{60}O_8(OH)_{28}Na_{10}$ and for BuckyUSA PHF as $C_{60}O_{16}(OH)_{10}Na_{24}$. The empirical formulas are consistent with the number of functional groups added to fullerene cage as being in the range of 25 to 42; however, the PERC PHF displayed a higher number of functional groups per molecule than BuckyUSA PHF.

TGA Analysis

Figure 6:
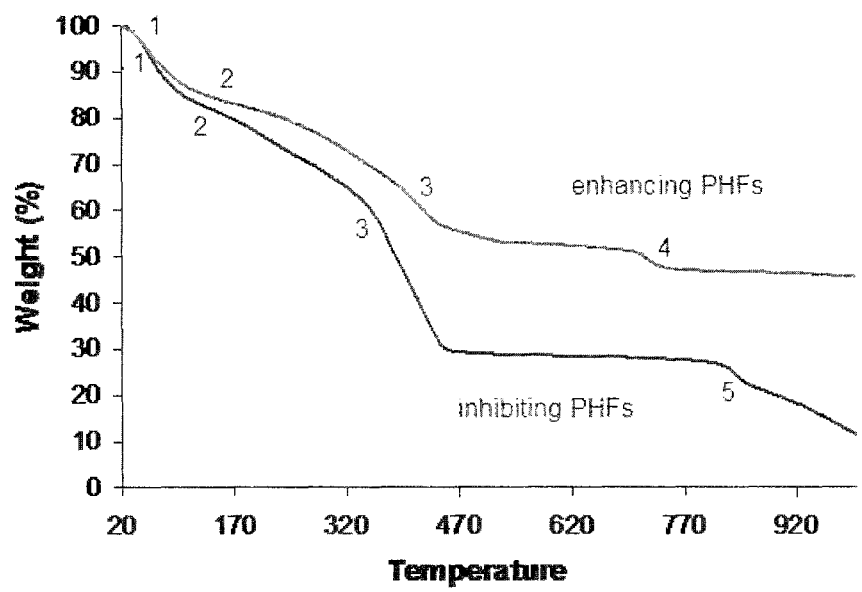
FIG. 6 shows thermal gravimetric analysis (TGA) spectra of PERC PHFs (enhancing) and BuckyUSA PHFs (inhibiting).

Thermo gravimetric analyses (TGA) of PERC and BuckyUSA PHF samples are presented in FIG. 6. The weight loss generally occurs in 4 or 5 stages. The first stage of weight loss is attributed to desorption of physically adsorbed water and accounted for 16% of the weight of both PHF samples. The second stage is attributed to desorption of hydroxyl functional groups and was 20% and 21% of the weight of PERC and BuckyUSA PHF, respectively. The weight loss in stage 3 is attributed to desorption of hemiketal functional groups and accounted for 11% of weight of PERC PHF and 34% of the weight of BuckyUSA PHF. A small weight loss (6%) in stage 4 was observed for PERC PHF and is attributed to desorption of carbonyl or epoxide groups. No weight loss in stage 4 was observed in BuckyUSA PHF, suggesting an absence of carbonyl or epoxide groups. BuckyUSA PHF exhibited thermal degradation of structure resulting in further 19% weight loss, stage 5. No loss in stage 5 was observed for PERC PHF. The total weight loss up to a temperature of 1,000° C. was 54% for enhancing PHF. TGA shows that the ratio of the weights of hemiketal to hydroxyl groups is higher for BuckyUSA PHF. A higher proportion of hemiketal to hydroxyl groups was also observed by XPS.

Where R is defined as the ratio of other functional groups to hydroxyl groups, as determined by XPS analysis, the values of R for PERC and BuckyUSA PHF are 0.27 and 1.66, respectively. The higher R for the BuckyUSA PHF correlates to a lower stability PHF, as observed by thermal degradation at temperatures greater than 800° C., as indicated in FIG. 6.

Enhancement of Electron Scavenging Ability of PHF

Enhancement of the electron scavenging ability of PHFs by controlling the composition of the PHFs was undertaken by comparing dye degradation in the presence of different PHFs with $TiO_2$.

Photocatalytic Dye Degradation

Dye degradation experiments were conducted with anatase (5 nm, Alfa-Aesar) titanium dioxide as the photocatalyst. A photocatalyst suspension was prepared by sonicating 30 mg/L of anatase for 1 hour. PHF was added to the suspension to give a final concentration of 0.03 mg/L. The dye, Procion Red MX5B, was added to the photocatalyst suspension to give a final concentration of 3 mg/L. The reaction mixture was transferred to a Petri dish with a magnetic stirrer and placed 100 mm below a bank of 16 UVA lamps (Southern New England Ultra Violet Company, Branfield, Conn.). The mixture was stirred in the dark for 10 minutes and then exposed to UVA at an intensity of 86 W/m$^2$. Immediately prior to turning on the lights, two 1.5 mL samples were transferred using a pipette into plastic vials. Subsequent samples were collected at 15 minute intervals for one hour. Each collected sample was centrifuged twice at 10,000 g for 15 minutes and the final supernatant was transferred to a plastic (PMMA) cuvette. UV-Vis spectra were obtained, and the absorbencies at 512 nm and 538 nm were used for data analysis. The log of normalized sample absorbance was plotted against irradiation time and the slopes measured to obtain pseudo-first order degradation coefficients.

Figure 7:
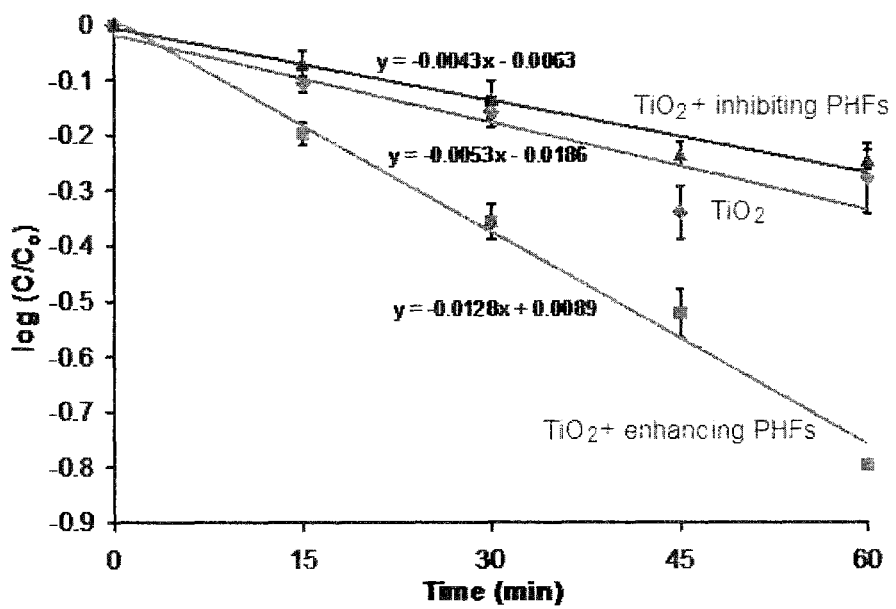
FIG. 7 shows first-order degradation kinetics plots for Procion Red MX-5B under UVA irradiation using $TiO_2$, $TiO_2$ with BuckyUSA PHFs (enhancing), and $TiO_2$ with PERC PHF (inhibiting) as photocatalysts. Error bars represent plus or minus 1 standard deviation.

Photocatalytic degradation studies of Procion Red dye with $TiO_2$ free of PHFs, $TiO_2$ combined with PERC PHFs, and $TiO_2$ combined with BuckyUSA PHFs are presented in FIG. 7, which plots the first order degradation of the dye over the period of an hour. The ratio of PHF to $TiO_2$ was set to a value of 0.001. The activity of PHF was determined by its ability to enhance the rate of photocatalytic degradation of the dye. The pseudo-first order rate coefficient for $TiO_2$ with PERC PHF (0.0128±0.0029 min$^{-1}$) was 2.6 times higher than the rate coefficient for $TiO_2$ without PHF (0.0048±0.0005 min$^{-1}$). Presence of BuckyUSA PHF gave a somewhat inhibited photocatalytic rate that was lower but not significantly different ($\alpha$=0.05) than $TiO_2$ free of PHFs.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. An enhanced photocatalyst comprising:
   $TiO_2$ or ZnO nanoparticles; and
   polyhydroxyfullerenes (PHFs) comprising a fullerene ($C_n$) with a multiplicity of hydroxyl substituents on said fullerene, wherein n is 20 to 500 and having a ratio of non-hydroxyl functional groups to hydroxyl functional groups that is less than or equal to 0.3, wherein said PHFs have an average of about 27 to about 48 functional groups per 60 carbon atoms.

2. The photocatalyst of claim 1, wherein the weight loss upon heating the dry PHFs of the photocatalyst to a temperature of 1,000° C. is less than 60 percent by weight.

3. The photocatalyst of claim 1, wherein said $TiO_2$ nanoparticles are about 2 to about 100 nm in diameter.

4. The photocatalyst of claim 1, wherein said PHFs have a carbon cage that comprises $C_{60}$, $C_{70}$, $C_{80}$ or their mixtures.

5. The photocatalyst of claim 1, wherein a weight ratio of said PHFs to said $TiO_2$ nanoparticles is about 0.001 to about 0.003.

6. A method of photo chemically decontaminating a surface or a fluid medium in contact with the surface comprising the steps of:
   providing to a surface a photocatalyst according to claim 1, wherein photocatalytic activity of said photocatalyst is more than twice of said $TiO_2$ nanoparticles free of PHFs towards degradation of a chemical or bacteriological contaminant; and
   irradiating said photocatalyst with ultraviolet (UV) or visible light.

7. The method of claim 6, wherein said photocatalyst is provided as an aqueous suspension.

8. The method of claim 7, wherein said step of providing comprises spraying said suspension on said surface.

9. The method of claim 6, wherein said $TiO_2$ nanoparticles are about 2 to about 100 nm in diameter.

10. The method of claim 6, wherein said PHFs have a carbon cage that comprises $C_{60}$, $C_{70}$, $C_{80}$ or any mixture thereof.

11. The method of claim 6, wherein a weight ratio of said PHFs to said $TiO_2$ nanoparticles is about 0.001 to about 0.003.

12. The method of claim 6, wherein said step of irradiation comprises exposure of said photocatalyst to sunlight.

13. The method of claim 6, wherein said step of irradiation comprises exposure of said photocatalyst to a visible or an ultraviolet lamp.

14. An active film for a heterojunction organic solar cell, comprising:
   a conjugated polymer; and
   polyhydroxyfullerenes (PHFs) comprising a fullerene ($C_n$) with a multiplicity of hydroxyl (OH) substituents on said fullerene, wherein n is 20 to 500 and having a ratio of non-hydroxyl functional groups to hydroxyl functional groups that is less than or equal to 0.3, wherein said PHFs have an average of about 27 to about 48 functional groups per 60 carbon atoms, and wherein said conjugated polymer is a polythiophene, substituted polythiophene, polyvinylenephenylene substituted polyvinylenephenylene, polybenzothiadiazole, substituted polybenzothiadiazole, polypyrroles, substituted polypyrroles and regular or random copolymers thereof.

15. An organic semiconductor for an organic thin-film field effect transistor (FET) comprising polyhydroxyfullerenes (PHFs) comprising a fullerene ($C_n$) with a multiplicity of hydroxyl (OH) substituents on said fullerene, wherein n is 20 to 500 and having a ratio of non-hydroxyl functional groups to hydroxyl functional groups that is less than or equal to 0.3, wherein said PHFs have an average of about 27 to about 48 functional groups per 60 carbon atoms, wherein said FET is n-channel.

16. The organic semiconductor of claim 15, further comprising p-channel conducting polymers, wherein said FET is ambipolar.

\* \* \* \* \*